United States Patent
Freyman et al.

(10) Patent No.: US 7,579,189 B2
(45) Date of Patent: Aug. 25, 2009

(54) ALIGNED SCAFFOLDS FOR IMPROVED MYOCARDIAL REGENERATION

(75) Inventors: Toby Freyman, Waltham, MA (US); Maria Palasis, Wellesley, MA (US); Mark Ungs, Minnetonka, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 12/111,482

(22) Filed: Apr. 29, 2008

(65) Prior Publication Data
US 2008/0260798 A1 Oct. 23, 2008

Related U.S. Application Data

(62) Division of application No. 10/892,518, filed on Jul. 15, 2004, now Pat. No. 7,384,786.

(60) Provisional application No. 60/487,909, filed on Jul. 16, 2003.

(51) Int. Cl.
*C12N 5/00* (2006.01)
*A61K 9/00* (2006.01)

(52) U.S. Cl. .................. 435/395; 435/325; 424/400; 424/422; 424/443

(58) Field of Classification Search .............. 435/373, 435/395, 325; 424/400, 422, 443
See application file for complete search history.

(56) References Cited

U.S. PATENT DOCUMENTS 5,855,610 A 1/1999 Vacanti et al. ............. 623/2.13

FOREIGN PATENT DOCUMENTS

| WO | WO 97/41208 | 11/1997 |
| WO | WO 00/34442 | 6/2000 |

OTHER PUBLICATIONS

Badylack et al., "Small intestinal submucosa: A substrate for in vitro cell growth," *Journal of Biomaterials Science Polymer Edition*, 9(8):863-878, 1998.
Badylak et al., "Morphologic study of small intestinal submucosa as a body wall repair device," *Journal of Surgical Research*, 103(2):190-202, 2002.
Badylak et al., "Strength over time of a resorbable bioscaffold for body wall repair in a dog model," *Journal of Surgical Research*, 99(2):282-287, 2001.
Evans et al., "Novel 3D culture system for study of cardiac myocyte development," *American Journal of Physiology*, 285(2):H570-H578, 2003.
Lu S-H et al., "Muscle derived stem cells seeded into acellular scaffolds develop calcium-dependent contractile activity that is modulated by nicotinic receptors," *Urology*, 61:1285-1291, 2003.
Voytik-Harbin et al., "Small intestinal submocosa: A tissue-derived extracellular matrix that promotes tissue-specific growth and differentiation of cells in vitro," *Tissue Engineering*, 4(2):157-174, 1998.

*Primary Examiner*—Ruth A Davis
(74) *Attorney, Agent, or Firm*—Fulbright & Jaworski LLP

(57) ABSTRACT

The present invention relates to a biocompatible, three-dimensional scaffold useful to grow cells and to regenerate or repair tissue in predetermined orientations. The scaffold is particularly useful for regeneration and repair of cardiac tissue. The scaffold contains layers of alternating A-strips and S-strips, wherein the A-strips within each layer are aligned parallel to each other and preferentially promote cellular attachment over attachment to the S-strips. Methods of producing and implanting the scaffold are also provided.

23 Claims, 2 Drawing Sheets

US 7,579,189 B2

ALIGNED SCAFFOLDS FOR IMPROVED MYOCARDIAL REGENERATION

The present application is a divisional of application Ser. No. 10/892,518, filed Jul. 15, 2004, now U.S. Pat. No. 7,384,786 which claims the benefit of priority to U.S. Provisional Application Ser. No. 60/487,909, filed Jul. 16, 2003, the entire contents of each of which are hereby incorporated by reference in their entirety.

BACKGROUND OF THE INVENTION

Biocompatible and biodegradable scaffolds are used in tissue reconstruction and repair. The scaffold, for example, can serve as both a physical support and adhesive substrate for cells during in vitro culturing and subsequent implantation in vivo. Scaffolds are utilized to deliver cells to desired sites in the body, to define a potential space for engineered tissue, and to guide the process of tissue development. Cell transplantation on scaffolds has been explored for the regeneration of skin, heart, nerve, liver, pancreas, cartilage, and bone tissue using various biological and synthetic materials. Scaffolds have also been implanted directly into patients without prior culturing of cells in vitro. In this case, the initially cell-free scaffold needs to be designed in a manner that cells from the surrounding living tissue can attach to the scaffold, migrate into it and form functional tissue.

Synthetic materials, such as polyester fiber (e.g., DACRON™) or polytetrafluoroethylene (PTFE) (e.g., TEFLON™), have been extensively used as implants to replace diseased or damaged body parts. However, these materials have enjoyed limited success because of their poor biocompatibility. Synthetic materials frequently cause persistent inflammatory reactions and are further limited by their lack of biodegradation, which results in the failure of the body to integrate and/or remodel these materials into the surrounding tissue. Other synthetic materials that are more biodegradable than polyester fibers or PTFE have been used to fabricate tissue-engineering scaffolds such as polyglycolic acid (PGA), polylactic acid (PLA). PGA, PLA and their copolymers are the most commonly used synthetic polymers in tissue engineering. However, in order for these structures to promote functional tissue growth/reconstruction, a complex micro-architecture must be produced, and this requires difficult processing methods.

Non-synthetic materials, such as animal materials, have also been used to produce tissue-regeneration/repair scaffolds. Efforts to use animal materials have been unsatisfactory when these materials are cross-linked by formaldehyde or glutaraldehyde, for example. This form of generalized aldehydic crosslinking tends to render biomaterials sufficiently unrecognizable to tissue cells such that normal remodeling and integration are not promoted. Similarly, other types of chemical processing of animal or human biomaterials, such as extraction with detergents, hypertonic buffers or hypotonic buffers can alter them to the degree that leave these biomaterials toxic to tissue cells, ineffective in promoting angiogenesis, and ineffective in stimulating repair and remodeling processes needed for the conversion of an implant into a functional substitute for the tissue or organ being replaced.

Another approach uses extracellular matrix (ECM) components in processed or natural forms to regenerate tissue in vitro and in vivo. The interaction of cells with ECM in in vivo and in vitro environments is important in the organization, function and growth of all tissues and organs. Biochemical and biophysical signals between the cell and the ECM regulate fundamental cellular activities including adhesion, migration, proliferation, differential gene expression, and programmed cell death. Processed forms of ECM have been used as tissue regeneration aids. For example, as described in U.S. Pat. No. 5,275,826, fluidized intestinal submucosa can be injected into host tissues in need of repair or used in combination with other graft materials. Basement-membrane-derived ECM compositions (e.g. MATRIGEL™, BECTON-DICKINSON) in the form of polymerizable extracts have also been used to regenerate or repair tissue. These polymerizable extracts can be formed or molded into a three-dimensional gel structure attempting to resemble lamellar structures (U.S. Pat. No. 4,829,000). Collagen-based gels have also been combined with specialized cells. This process depends upon interactions between the cells and collagen filaments in the gel so that the cells condense and organize. While tissue-like constructs have been fabricated and been shown to have some resemblance to their natural counterparts, these constructs do not readily develop the matrix complexity characteristic of the actual tissues that they are meant to imitate (U.S. Pat. Nos. 4,485,096 and 4,485,097).

Natural forms of ECM (e.g., isolated sheets or layers) can be obtained from tissue submucosa of warm-blooded vertebrates. For example, the tunica submucosa of the intestine is often used as tissue graft material; see U.S. Pat. Nos. 4,902,508 and 5,281,422. Both stomach (U.S. Pat. No. 6,099,567) and urinary bladder (U.S. Pat. Nos. 5,554,389 and 6,171,344) submucosa have also been described as natural sources of ECM. Large sheets of submucosal tissue can be prepared from smaller segments of submucosal tissue through conventional techniques such as weaving, knitting or the use of adhesives (U.S. Pat. No. 5,997,575). Purified submucosa can also be shaped into other forms with other graft materials, for example, a tubular graft composed of sheets of submucosa wrapped around a tube (U.S. Pat. No. 6,358,284). However, a limitation of these natural forms is that it is difficult to fashion three-dimensional tissue structures that mimic the endogenous tissue architecture where the graft or scaffold is to be used, for example, to form the complex shape of a valve.

Cardiac tissue repair presents challenges to tissue-engineering methods. Cardiac tissues are difficult to repair as the tissue has a limited ability to regenerate and because the tissue has a complex architecture that is difficult to mimic. For example, cardiomyocytes have a natural complex architecture with particular electromechanical properties. Endogenous cardiomyocytes are organized into parallel cardiac muscle fibers with intracellular contractile myofibrils oriented parallel to the long axis of each cell. Junctional complexes between abutting cells are concentrated at the ends of each cardiomyocyte. Such architecture provides the electromechanical coupling of cardiomyocytes needed to stimulate the transmission of directed contraction over long distances. However, cultured cardiomyocytes typically spread on a flat substrate to form an unorganized monolayer with disorganized myofibrils and junctions. In vitro methods have been created that align cardiomyoctes into functional organizations by growing cultured cardiomyocytes on flat micro-patterned substrates (McDevitt, T. C. et al., "In vitro generation of differentiated cardiac myofibers on micropatterned laminin surfaces," *J. Biomed. Mater. Res.*, (2002), 60:472-479). However, such methods provide two-dimensional tissue layers that are difficult to transform into a three-dimensional tissue repair scaffold.

Thus, biocompatible, biodegradable, three-dimensional scaffolds that are adaptable to different in vivo tissue architectures and that promote the natural, functional coupling between cells present in the scaffold and cells in the surrounding tissue are desired. Further, methods of producing such improved scaffolds that are efficient and simple are also desired.

SUMMARY OF THE INVENTION

The present invention is directed to a semi-solid, three-dimensional, biocompatible scaffold for cell growth, tissue repair or regeneration, comprising one or more layers of alternating attachment-strips ("A-strips") and separating-strips ("S-strips") wherein the A-strips within each layer are aligned parallel to each other and preferentially promote cellular attachment over attachment to the S-strips. The present invention is also directed to methods of producing and implanting such scaffolds.

In one aspect, the scaffold is biodegradable and re-shapeable. After implantation of the scaffold into an area of tissue damage or disease, cells migrate into the scaffold and preferentially attach to the A-strips allowing cells to align in accordance with the architecture of the scaffold. The architecture of the scaffold can thus provide spatial- and orientation-dependent signals for cell growth and/or differentiation. As the cells grow and differentiate, they reshape the architecture of the scaffold such that the scaffold is adopted into the surrounding tissue. Eventually these scaffolds completely degrade leaving behind the integrated cellular tissue and tissue-specific extracellular matrix.

The design of the scaffolds can be varied in relation to different tissue architectures by varying the dimensions of the elements of the scaffolds, and/or the materials that the elements of the scaffold are made of. The elements of the scaffold are the A-strips, S-strips and the separating layers, and their dimensions as to width, length, thickness and porosity are fixed according to a scaffold's intended use in the repair, regeneration or growth of a particular tissue or cell type, in vivo or in vitro. The width of the A-strips and S-strips are fixed to promote the ordered alignment of cells within a layer so that cells can receive spatial- and orientation-dependent signals for cell growth and/or differentiation from each other and from the strip materials. The materials of the scaffold are also chosen such that the A-strips promote the adhesion of cells more than the S-strips and the separating layers, and such that the porosity of the S-strips and separating layers allow a homogeneous distribution of cells throughout the scaffold. Further, the scaffold can be supplemented or treated with bioactive agents such as those, for example, that promote cell migration and proliferation.

In accordance with the invention, the scaffold can be implanted in a subject at a site of tissue damage without having been pre-seeded with cells. In this embodiment, the scaffold is seeded with cells in situ either by endogenous cells or by cells separately implanted into the subject. Alternatively, the scaffold can be pre-seeded with cells in vitro prior to implantation in a subject.

In another aspect of the present invention, methods of producing the scaffolds of the inventions are provided. In one embodiment, a method of producing a semi-solid, three-dimensional, biocompatible scaffold comprises layering one or more sheets of biocompatible strip material by a fixed distance from each other; cutting the sheets to provide A-strips of a fixed width, maintaining the parallel A-strips at a fixed distance from each other; and contacting the parallel A-strips with a biocompatible material that does not promote cellular attachment under conditions to fill the space separating the A-strips, thereby forming S-strips, and to fill the space separating the layers; to form a semi-solid, three-dimensional, biocompatible and, preferably, biodegradable scaffold.

BRIEF DESCRIPTION OF THE DRAWINGS

FIG. 1A is a side-view and FIG. 1B presents a top-view. In this figure, several sheets of submucosal tissue (denoted by the black lines) are clamped with the sheets separated by a fixed horizontal distance. A 'comb of knives' is inserted vertically through all the sheets and moved along their length to create A-strips. A spacer comb ("spacers" in the figures) is inserted at the end where the cutting begins and another spacer comb follows the comb of knives, and remains at the other end after the cutting is completed. These spacer combs thus hold the A-strips apart by a fixed distance. The clamped and spaced A-strips are then placed into a mold filled with an alginate solution. A cross-linking agent is added to the alginate solution. The clamps and spacer combs are removed once the scaffold attains a semi-solid state and results in formation of a semi-solid scaffold containing the aligned A-strips of submucosa separated by alginate S-strips.

FIG. 1B additionally depicts the dimensions of the apparatus. The width of the sheet is represented by "a", and the width of a scaffold layer is represented by "b". The width of a scaffold layer, "b", can be determined by the formula "b=a+(n)(s)" where "n" represents the number of knives in a comb of knives and where "s" represents the width of the spacer in the comb of spacers. The knife spacing can be determined from the formulas: "a/n+1" or "(b−(n)(s))/(n+1)".

DETAILED DESCRIPTION OF THE INVENTION

Figure 1A:
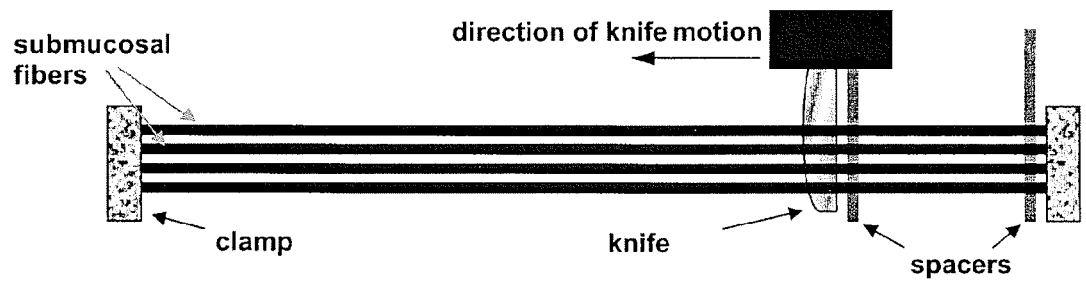
FIG. 1A and FIG. 1B depict an apparatus that can be used to produce scaffolds in accordance with the present invention.

The issued U.S. patents, published and allowed applications, and references cited herein are hereby incorporated by reference.

The present invention relates to a biocompatible, three-dimensional scaffold useful for growing cells, regenerating or repairing tissue. This invention also provides methods of producing and implanting the scaffold. The semi-solid, three-dimensional, biocompatible scaffold for cell growth, tissue repair or regeneration, or any combination thereof, comprises one or more layers of alternating attachment-strips ("A-strips") and separating-strips ("S-strips"), wherein the A-strips within each layer are aligned parallel to each other, and wherein the A-strips preferentially promote cellular attachment. "Attachment-strips" or "A-strips" are defined herein as an element of the scaffold that preferentially promotes cellular attachment over other elements of the scaffold. "Separating-strips" or "S-strips" are defined herein as an element of the scaffold that does not preferentially promote cellular attachment, and in relation to the architecture of the scaffold, serves to separate the A-strips from each other within a scaffold layer.

The dimensions and the materials of the scaffold are designed to allow cells to align in a manner to receive spatial- and/or orientation-dependent cues or signals from other cells and/or from the materials that constitute the A-strips of the scaffold. These signals or cues help the cells in the scaffold to grow and differentiate so that the cells can adopt to and/or integrate into the surrounding tissue in which the scaffold is implanted. Additionally, the scaffold can also provide the cues or signals such that cells in the scaffold grow and differentiate into functional tissues in vitro.

A. Structure and Materials of the Scaffold

The scaffold of the present invention has from one to many layers. Preferably the scaffold comprises multiple alternating layers of scaffold layers and separating layers. The scaffold layer is composed of alternating A-strips and S-strips where the A-strips within the scaffold layer are aligned parallel to each other. In accordance with the invention, A-strips preferentially promote the attachment of cells, and S-strips and separating layers do not preferentially promote the attachment of cells. As used herein, "preferentially promotes" means that more cells attach to the A-strips rather than to the S-strips or the separating layers. In addition, preferentially promoting attachment can be achieved by preferential proliferation or differentiation of the cells on the A-strips rather than on the S-strips or the separating layers.

It is preferred that greater than about 70% of the cells within a scaffold are present on A-strips. It is more preferred that greater than about 90% of the cells within a scaffold are present on A-strips. The percentage of cells present on A-strips as compared to S-strips can be tested by performing a 2-dimensional cell culture experiment where the culture surface is coated with S-strip and A-strip material in an area and design similar to one layer of a desired scaffold. A cell type will be used which is relevant to the intended target tissue of the scaffold.

The A-strips can range from about 20 micrometers to about 200 micrometers in thickness, and from about 20 micrometers to about 100 micrometers in width. These dimensions, especially the width, are relevant to the cell-attachment properties of the A-strip. For example, if the A-strips are too narrow (i.e., if the A-strips are more narrow than the size of a cell), then cells cannot properly attach. If the A-strips are too wide, then cells may not properly or efficiently align in relation to the architecture of the layer because the cells cannot align on the A-strips in a linear fashion. For use with cardiomyocytes, the preferred width of the A-strips is from about 20 to about 50 micrometers in width.

The S-strips can range from about 20 micrometers to about 200 micrometers in thickness, and from about 20 micrometers to about 200 micrometers in width. If the S-strips are too narrow, i.e., similar to the width of a single cell, then the A-strips cannot function to align the cells in a parallel orientation. For example, if the cells on one A-strip are able to span the distance of the S-strip to another A-strip, then the A-strips are less effective in aligning cells in a substantially linear fashion on an A-strip. For cardiomyocytes, the preferred width of an S-strip is from about 50 to about 100 micrometers in width.

The separating layer alternates with the scaffold layer. As defined herein, a "scaffold layer" is a layer of a scaffold comprising alternating A-strips and S-strips. In other words, the separating layer serves to separate the scaffold layers from each other. According to the present invention, a separating layer can be made of a material suitable for a S-strip. Hence, a separating layer is made of a material that does not preferentially promote cell attachment and/or proliferation and/or differentiation. Thus, the A-strips of the scaffold preferentially promote cell attachment over the S-strips and the separating layers.

The separating layer can range from about 20 micrometers to about 200 micrometers in thickness. Further, the separating layer and the S-strips can, but need not necessarily contain pores. The pores allow cell migration and can range from about 10 micrometers to about 300 micrometers in diameter. The pore size cannot exceed the dimensions of a layer. The pores allow cells to migrate throughout the scaffold, to aid in providing an even or homogeneous distribution of cells throughout the scaffold. The pores also enable the migration of soluble peptides and proteins that are necessary for cellular growth and communication. The pores also enable efficient vascularization between the scaffold and the surrounding tissue.

Figure 2:
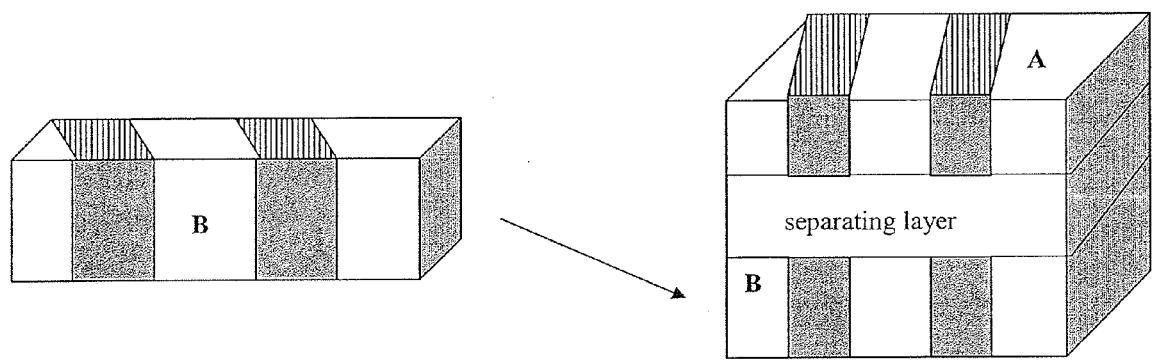
FIG. 2 depicts a scaffold where the strips between layers are not aligned. Lined areas represent A-strips and clear areas represent S-strips. In this figure, scaffold layer B is made separately, and then combined with scaffold layer A and a separating layer to form a multi-layered scaffold. The A-strips of layer A can be placed in any orientation relative to the A-strips of layer B in the scaffold.

The alignment of the A-strips within a scaffold layer is parallel. However, when the scaffold is multi-layered, the alignment of the A-strips between successive scaffold layers need not be parallel (See FIG. 2). For example, the scaffold can be constructed such that there is no overall alignment of the A-strips from scaffold layer to scaffold layer. This overall random alignment serves to grow and regenerate tissue where cell alignment is not ordered, for example, in skin. Of course, the scaffold can be constructed such that all the A-strips are aligned in one general parallel orientation, or in any other desired pattern, e.g., such as alternating 90° angles.

The scaffold is preferably composed of a material that permits cells to reshape the scaffold. Such properties allow the cells of the scaffold to become integrated with or adopted into the surrounding tissue in which the scaffold is implanted. By "integrating" or "adopting", the cells of the scaffold are not rejected by the surrounding tissue in which the scaffold is implanted. The scaffold is more re-shapeable when the materials of the scaffold are biodegradable and not synthetic.

The A-strips of the present invention are constructed from a biocompatible substance that can be formed into a shape that essentially resembles a strip or a fiber having the dimensions stated herein. Biocompatible substances that can be used to form the A-strips, include but are not limited to, extracellular matrix material, proteins or peptides that are not present in extracellular matrices but have cell attachment properties, and synthetic materials, provided such materials can be formed into A-strips of the appropriate size and have the requisite biological characteristics to preferentially promote cell attachment and/or proliferation and/or differentiation. Non-synthetic, biocompatible and biodegradable materials are preferred for A-strips, such as extracellular matrix material. If synthetic materials are used as strip material, the synthetic materials can be combined with either extracellular matrix material or proteins or peptides with cell-attachment properties so that the strips preferentially promote cell attachment or proliferation.

According to the present invention, "extracellular matrix material" is any material or substance that is present in an extracellular matrix. An extracellular matrix is an acellular sheet or layer that consists of three major classes of biomolecules: (1) structural proteins such as collagen and elastin, (2) specialized proteins such as, perlacan, agrin, laminin, fibronectin, entactin, nidogen, and fibrillin, and (3) proteoglycans which are composed of a protein core to which is attached long chains of repeating disaccharide units (glycosaminoglycans (GAGs)). Thus, according to the present invention, any of the above-types of biomolecules, individually or in combination, in natural, processed or recombinant forms, are considered extracellular matrix material.

The extracellular matrix material can be isolated from animals or from an in vitro cellular source rich in producing extracellular matrix material. Sheets of extracellular matrix isolated from animals can be cut to form the A-strips of the scaffold. Alternatively, sheets of isolated extracellular matrix material can be processed into gels or liquids (see for example, U.S. Pat. Nos. 5,275,826 or 4,829,000), and these gels or liquids can be molded to form the A-strips of the scaffold. Additionally, recombinant forms of extracellular matrix materials can be used to form the strips of the scaffold.

The extracellular matrix material can be isolated from a variety of tissue sources, for example, essentially any submucosa. A submucosa is a layer of areolar connective tissue that lies beneath the mucosa. Examples of submucosa that can be used as a source of extracellular matrix material, include intestine submucosa, stomach submucosa, liver submucosa, and urinary bladder submucosa. Basement membranes can also be used as a source of extracellular matrix material. Basement membranes are thin, but continuous sheets that separate epithelium from stroma and surround nerves, muscle fibers, smooth muscle cells and fat cells. Additionally, tissues such as bone, bone marrow, cartilage and placenta can also be sources of extracellular matrix material. Further, embryonic and fetal cardiac tissue can be sources of extracellular matrix material. Representative processes that can be used to isolate extracellular matrix material from tissue are described in, Voytik-Harbin, S. L., "Three-dimensional extracellular matrix substrates for cell culture," *Methods Cell Biol.*, (2001), 63:561-81.

The tissue sources of extracellular matrix material can be isolated from any mammal, including but not limited to: pig, human, cow, sheep, goat, donkey, horse, rabbit, dog, cat, rat and mouse. The extracellular matrix material can be in the form of a sheet from which A-strips are cut, or the material can be processed into their separate components or combinations of components, and then formed into A-strips or a sheet. Such sheets can then be cut into A-strips in accordance with the invention. Alternatively, if individual A-strips are formed, these A-strips have the dimensions as stated herein and are arrangeable in a parallel orientation.

Sheets of extracellular matrix can be isolated from essentially any type of submucosa. For example, in U.S. Pat. No. 4,902,508, by delaminating the tunica muscularis and at least the luminal portion of the tunica mucosa of the small intestine, a tunica submucosa was isolated. As described in U.S. Pat. No. 6,099,567, the stomach submucosa can be isolated by delaminating the smooth muscle layers of the muscularis externa and at least the luminal portion of the mucosal layer of a segment of the stomach. As described in U.S. Pat. No. 5,554,389, urinary bladder submucosa is isolated by delaminating the abluminal muscle cell layers and at least the luminal portion of the mucosal layer of a segment of urinary bladder. Acellular and detoxified sheets of submucosa are commercially available, for example, see COOK® Biotech Incorporated, SIS™ Technology (COOK Biotech Incorporated, 3055 Kent Avenue, West Lafayette, Ind. 47906 USA).

Extracellular matrix material can also be isolated as a slurry or solution. Solutions or slurries can be processed or molded into A-strips of the appropriate dimensions, for example, by the following processes: freeze-drying in a mold; air drying into A-strips; air drying into sheets which are cut into A-strips; gelled by neutralizing pH; and solutions or slurries can be combined with a second material (e.g., collagen, gelatin, self-assembling peptides) which can be solidified, cross-linked, or otherwise turned into a solid without affecting the biological activity of the extracellular matrix material.

Processed or recombinant forms of extracellular matrix materials can be used as A-strip material. For example, U.S. Pat. No. 4,829,000 reports a processed, reconstituted, basement-membrane-derived extracellular matrix composition (MATRIGEL™). Also, U.S. Pat. No. 5,275,826 reports fluidized forms of submucosa. Purified or recombinant forms of collagen, elastin, perlacan, agrin, laminin, fibronectin, entactin, nidogen, fibrillin, proteoglycans can be used as strip material, and are commercially available. For example, BD BIOSCIENCE™ offers a variety of ECM products that can be used in the present invention: BD Matrigel™ Basement Membrane Matrix, Collagen I ECM, Collagen III ECM, Collagen IV ECM, Collagen V ECM, Fibronectin ECM, Laminin ECM.

The extracellular matrix material can be from a syngeneic, allogeneic or xenogeneic source. When used as the material comprising the A-strips of the scaffold, the extracellular matrix material is acellular, and should not be recognized as "foreign" by a host's immune system, and therefore should not be rejected by the host. Further, the biocompatible materials that comprise the scaffold are substantially endotoxin free.

Proteins and peptides that have cell-attachment properties but are not present in extracellular matrices can also be used as A-strip material. Such proteins and peptides include, but are not limited to, vitronectin, polypeptides with the amino acid sequence arginine-glycine-aspartic acid ('RGD sequence'), and poly-L-lysine. According to the present invention, proteins and peptides that have cell attachment properties are proteins or peptides that bind to molecules on a cell surface with an affinity such that the binding is not transient.

Synthetic materials such as polylactic acid (PLA), polyglycolic acid (PGA), co-poly-lactic/poly-glycolic acid polymers (PLGA), can also be used as A-strip material, if a non-biodegradable scaffold is desired. If synthetic materials are used as A-strip material, the synthetic materials can be combined with either extracellular matrix material or proteins or peptides with cell-attachment properties so that the A-strips preferentially promote cell attachment. Preferably, the A-strips of the present invention are made from extracellular matrix material or proteins or peptides with cell attachment properties.

The S-strips and the separating layers of the invention are biocompatible and preferably biodegradable substances that do not preferentially promote cell attachment. Preferably, the S-strips and the separating layers do not permit cells to substantially attach. The material of the S-strips and the material of the separating layer do not have to be identical. Examples of S-strips and separating layer material include, but are not limited to, alginate, agarose, polylactic acid (PLA), polyglycolic acid (PGA), co-poly-lactic/poly-glycolic acid polymers (PLGA), gelatin, ethylene-vinyl acetate, fibrin, sucrose octasulfate, dextran, polyethylene glycol, polyacrylamide, cellulose, latex, polyhydroxyethylmethacrylate, nylon, Dacron, polytetrafluoro-ethylene, polystyrene, polyvinylchloride co-polymer, cat gut, cotton, linen, polyester, and silk. Alginate, agarose and gelatin, are preferred. It is also preferred that all of the elements of the scaffold have a similar rate of biodegradation.

When the S-strips and separating layers comprise alginate, the porosity of alginate can be manipulated by using different sources of alginate, by varying the concentration of alginate, and by varying the divalent cations used to help polymerize the alginate.

Proteins or peptides can be micro-patterned on the surface of biocompatible sheets, A-strips, S-strips or separating layers. In the present invention, proteins or peptides are 'micropatterned' by immobilizing proteins or peptides in micrometer sized shapes on the surface of biocompatible materials.

Advances in patterning technology have generated a range of techniques with which biomolecules can be immobilized on surfaces with microscale precision. Some techniques that can be used with the present invention include microcontact printing, photolithography, photochemistry, 3D printing, and microwriting. These techniques are known to those of skill in the art.

The scaffold of the present invention can also be treated with bioactive agents. These agents can be used alone or in combination and include, but are not limited to, vascularization-promoting factor, a cytokine, a growth factor, an enzyme, a hormone, an angiogenesis factor, a vaccine antigen, an antibody, a clotting factor, a regulatory protein, a transcription factor, a receptor, a structural protein, and any functional fragment, variant or combinations thereof. Preferably, the agents are located on or in the A-strips of the scaffold, although they can be present in the S-strips and the separating layers, provided they do not alter the overall characteristic of the scaffold to promote cellular attachment to the A-strips. Agents that recruit cells or direct cells include cytokines, growth factors, enzymes, hormones, angiogenesis factors, regulatory proteins, transcription factors, receptors, structural proteins and any of their bioactive functional fragments. Agents that promote cell attachment include receptors and structural proteins. Agents that promote vascularization of the scaffold and tissue include vascularization promoting factors, cytokines, growth factors and angiogenesis factors.

Examples of specific bioactive agents include, but are not limited to, collagen, laminin, fibronectin, granulocyte-colony stimulating factors (G-CSF), granulocyte-macrophage colony stimulating factor (GM-CSF), stem cell factor (SCF), vascular endothelial growth factor (VEGF), platelet-derived growth factor (PDGF), transforming growth factors, human growth hormone (hGH), Factor VIII, Factor IX, erthropoietin (EPO), albumin, heme oxygenase, hemoglobin, alpha-1 antitrypsin, calcitonin, glucocerebrosidase, low density lipoprotein (LDL) receptor, IL-2 receptor, globins, immunoglobulins, catalytic antibodies, interleukins, chemokines, insulin, insulin-like growth factor 1 (IGF-1), insulinotropin, parathyroid hormone (PTH), leptin, an interferon, nerve growth factors, epidermal growth factor (EGF), endothelial cell growth factor, endothelial cell stimulating angiogenesis factor (ESAF), angiogenin, tissue plasminogen activator (t-PA), follicle stimulating hormone (FSH), Flt-3 ligand, megakaryocyte growth and development factor (MGDF), and 3-hydroxy-3-methyl glutaryl coenzyme A (HMG CoA) reductase inhibitors, and any functional fragment, variant or combinations thereof.

The architecture of the scaffold helps in promoting cellular growth and differentiation. Most cells can grow in vitro without any scaffolding. Yet, many cells do not fully differentiate without spatially defined cell-contact and orientation signals. For example, integrin receptors on the surface of cells bind to RGD (arginine-glycine-aspartic acid) sequences in extracellular matrix proteins such as fibronectin. This interaction induces cell spreading and intracellular signaling. Spatial orientation helps to provide proper cell-to-cell signaling and cellular function. For example, cardiomyocytes are organized into parallel cardiac muscle fibers with intracellular contractile myofibrils oriented parallel to the long axis of each cell and junctional complexes between abutting cells concentrated at the ends of each cardiomyocyte. Without this highly oriented architecture, electromechanical coupling of cardiomyoctes does not occur, and the transmission of directed contraction over long distances is not possible. Thus, although cardiomyocytes can be grown in in vitro cultures, the cultured cardiomyocytes only spread to form an epithelioid sheet, with disorganized myofibrils and diffuse intercellular junctions.

B. Cellular Growth, Tissue Repair and Regeneration

The scaffolds of the present invention are used for both in vitro and in vivo cellular growth and differentiation. The purpose of in vivo use is for the repair and regeneration of damaged and/or diseased tissue. The scaffolds can be used as self-seeding scaffolds for cellular attachment, growth and repair in situ; or the scaffold can be seeded in vitro with cells prior to implantation. Generally, cells at a concentration of $1 \times 10^6$ to $5 \times 10^6$ cells/ml are added to a dish or bioreactor containing a scaffold(s), and the cells are incubated for 24-72 hours at 37° C. at 5% $CO_2$ for initial seeding. However, the cell concentration can range from about $1 \times 10^4$ to about $1 \times 10^7$, or higher for cells that can achieve such concentrations.

As used herein, the term "damaged or diseased tissue" means tissue in which cells have been lost or have died due to insufficient blood supply, mechanical injury, infection, irradiation, trauma, disease, or other insult. For example, damaged and or diseased tissue includes, but is not limited to, scar tissue, and tissue that is torn, crushed, or has undergone necrosis resulting from blood loss. By "necrosis" is meant pathologic cell death following irreversible damage to the cell. The damaged or diseased tissue can be distinguished from the surrounding tissue, for example, by physical inconsistency or discontinuity.

Cells which can used to seed the scaffold in vitro include, but are not limited to, side population (SP) adult stem cells. Lineage negative ($Lin^-$) stem cells, $Lin^-CD34^-$ stem cells, $Lin^-CD34^+$ stem cells, $Lin^-cKit^+$ stem cells, mesenchymal stem cells (MSC), cord blood cells, tissue stem cells, whole bone marrow, bone marrow mononuclear cells (BM-MNCs), cardiac stem cells, tissue stem cells, endothelial progenitor cells (EPCs), skeletal myoblasts (satellite cells), muscle derived cells (MDCs), go cells, endothelial cells, adult cardiomyocytes, fibroblasts, smooth muscle cells, genetically modified cells, MyoD scar fibroblasts, pacing cells, embryonic stem cell clones, embryonic stem cells, fetal or neonatal cells, teratoma cells, and any combination thereof.

SP cells can be isolated by a fluorescence-activated cell sorter (FACS) technique utilizing the ability of SP cells to exclude Hoechst dye from the nucleus. In addition to bone marrow, SP cells have been isolated from most tissues, including cardiac and skeletal muscle. By the more common surface identification, these cells are $Lin^-$, $Sca-1^+$, $c-Kit^+$, $CD43^+$, $CD45^+$, $CD34^-$.

Bone marrow cells are isolated, and all the cells that have differentiated to a specific lineage are removed, either by FACS sorting or magnetic-bead sorting. The cells that remain are the stem and progenitor cells, or $Lin^-$ cells. Of these cells, the most primitive bone marrow-derived stem cells are $Lin^-CD34^-$. Cells that are $Lin^-CD34^+$ include hematopoietic stem cells. $Lin^-cKit^+$ cells express cKit, which is the cell surface receptor for stem cell factor. Therefore, $Lin^-cKit^+$ cells are often used as a stem cell population. $Lin^-cKit^+$ cells have been isolated from the heart and the bone marrow.

Whole bone marrow can be used for transplantation and scaffold seeding. The whole bone marrow sample is filtered to remove bone particles. Whole bone marrow includes many extracellular matrix proteins and growth factors. The BM-MNC population can be separated from whole bone marrow by a density gradient centrifugation procedure. The BM-MNC population contains non-granular white blood cells, progenitor cells, and stem cells. Although most work to date has focused on isolating stem cells from the bone marrow, some stem cells (e.g., SP, $Lin^-cKit^+$) can be isolated from tissues, for example fat and cardiac muscle.

MSCs are stem cells that ordinarily differentiate into the cells of mesenchymal tissues (e.g. bone, cartilage, fat), but can also differentiate into cardiomyocytes under certain conditions. MSCs are isolated from the bone marrow, and have the capacity to proliferate in vitro. EPCs are also isolated from the bone marrow based on cell surface markers. EPCs differentiate into endothelial cells, and when transplanted to ischemic tissue, these cells can form new blood vessels.

Cord blood cells are isolated from the blood remaining in the umbilical vein following child birth. This blood has been shown to contain immature stem cells or progenitor cells.

Skeletal myoblasts are cells responsible for the regeneration of skeletal muscle following injury. These cells have the ability to fuse with other myoblasts or damaged muscle fibers. In the present invention, skeletal myoblasts can be seeded into the scaffold so that these cells can integrate into a host's damaged myocardium or other damaged muscle tissue, and improve tissue properties or functionally participate in contraction. MDCs are a population of cells isolated from adult skeletal muscle that are similar to myoblasts, and can also be used to seed scaffolds that are to be implanted in areas of muscle damage. Go cells are also isolated from adult skeletal muscle, and these non-satellite cells express GATA-4 and, under in vitro growth conditions, develop into spontaneously beating cardiomyocyte-like cells.

When the scaffold is not seeded with cells prior to implantation of the scaffold, the scaffold serves as an in situ self-seeding implant. After implantation of the scaffold into an area of tissue damage, cells migrate into the scaffold and preferentially attach to the A-strips. The cells are aligned to the architecture of the scaffold. As the cells grow and differentiate, they are able to refashion the architecture of the scaffold such that the scaffold is adopted into the surrounding tissue. When all the materials of the scaffold are biodegradable, the scaffold completely degrades leaving behind only the integrated cellular tissue and tissue-specific extracellular matrix.

The scaffold of the present invention can be designed to grow and/or repair any cell or tissue type in vitro or in vivo. If, for example, the scaffold is used to grow a skin substitute in vitro, the scaffold is designed so that the scaffold layers are randomly aligned relative to each other. If, for example, the scaffold is used to repair and regenerate damaged myocardial tissue, then the scaffold can be designed such that the scaffold layers are all substantially aligned relative to each other in a parallel orientation.

Following implantation of the seeded or non-seeded scaffold into a subject, the subject can be treated with bioactive agents in order to promote the proliferation and differentiation of cells in the scaffold. Preferred bioactive agents for subject treatment include GM-CSF, G-CSF, IL-1, IL-3, SCF, VEGF, Flt-3 ligand, heme oxygenase, cell survival factors, and attachment factors such as collagen, laminin, fibronectin, and fragments and variants thereof which retain the same biological activity including fusion proteins and chimeric proteins. Chemical agents, such as nitric oxide and 5-azacytidine can also be used to promote engraftment of scaffolds. Alternatively, the scaffolds of the present invention can be pretreated to contain bioactive agents or chemical agents.

A subject to be treated according to the method of the invention is one who has suffered an injury or has an illness or disorder that results in damaged or diseased tissue. In certain cases, the injury is an infarction that results in tissue necrosis, and more particularly, a myocardial infarction. Such subjects include humans and animals, such as laboratory animals or feed animals, including, but not limited to, mice, rats, rabbits, dogs, cats, cattle, swine, non-human primates, and others. Preferably, the subject is a human.

The scaffold can be used to treat any organ or tissue in need thereof. Examples of tissues include, but are not limited to, bone, cartilage, and striated muscle, which include cardiac muscle and skeletal muscle. Examples of organs that can be treated by the methods of the invention include, but are not limited to, heart, liver, brain, kidney, intestine, lung, eye, pancreas, bladder, and spinal cord.

The replacement of defective cardiac tissue by functioning myocardium is desired. Two strategies for the repair of cardiac tissue, the implantation of isolated cells and the implantation of in vitro designed tissue equivalents, are both improved when used with the scaffolds of the present invention.

In prior studies, the implantation or injection of cells into myocardial scar tissue improved global heart function (for example, see Carrier, R. L. et al., "Cardiac Tissue Engineering: Cell Seeding, Cultivation Parameters, and Tissue Construct Characterization," *Biotechnology and Bioengineering*, 1999, 64(5): 580-589; Folliguet, T. A., "Adult Cardiac Myocytes Survive and Remain Excitable During Long-Term Culture on Synthetic Supports," *J. Thorac. Cardiovasc. Surg.*, 2001, 121:510-519; Li, R. K. et al., "Cardiomyocytes transplantation improves heart function," *Annals of Thoracic Surgery*, 1996, 62:654-661; Li, R. K. et al., "In vivo survival and function of transplanted rat cardiomyocytes," *Circulation Research*, 1996, 78:283-288; Li, R. K. et al., "Survival and Function of Bioengineered Cardiac Grafts," *Circulation*, 1999, 100 (suppl. II): 63-69; and Li, R. K. et al., "Construction of a bioengineered cardiac graft," *J. Thorac. Cardiovasc. Surg.*, 2000, 119:368-375. Surprisingly, the effect appeared to be independent of cell origin, as positive results were reported from fetal or neonatal cardiac myocytes, fibroblasts, endothelial cells, smooth muscle cells, skeletal myoblasts, and stem cells. Further, expanding autologous skeletal myoblasts ex vivo and injecting them into the area of scar tissue has also led to some positive results. However, despite survival and differentiation of implanted cells, mechanical and electrical cell-cell contacts between graft and host, a requirement for functioning myocardial tissue, is only rarely observed. Thus, one embodiment of the present invention comprises implanting a scaffold (either with or without pre-seeding of cells or bioactive agents) to the area of myocardial scar tissue. Concurrently, subsequently or prior to implantation of the scaffold, cells are additionally implanted. The scaffolds of the present invention are designed such that mechanical and electrical cell-cell contacts between graft and host are improved.

The second approach for the repair/replacement of damaged or diseased cardiac tissue uses in vitro designed cardiac constructs. However, prior in vitro designed cardiac constructs have suffered the problems of: (1) the scaffold materials exhibit an intrinsic stiffness that compromises diastolic function, (2) biodegradation of the scaffold materials remains incomplete, adding to problems with diastolic function, (3) size limitation of engineered constructs due to a lack of metabolic or oxygen supply in the core of three-dimensional constructs, and (4) lack of homogeneous cell distribution within the scaffold. As to the last problem, cardiac myocytes seeded on or in gelatin meshes formed only a 300 micrometer thick cell layer on the outside due to problems of the myocytes in migrating through the gelatin meshes (Li et al., 2000). Similarly, cardiac myocytes seeded on synthetic polymer scaffolds only form cell layers of 50 to 70 micrometers.

In one embodiment, the scaffolds of the present invention remedy the above-stated problems. Because the scaffold can have multiple scaffold layers with A-strips that promote cell-attachment, and because the separating layers and S-strips can be designed to have specific pore sizes, homogeneous or even cell distribution within the scaffold is greatly improved over prior scaffolds. Additionally, the size is not as limited as prior constructs with the present scaffolds because the pores within the scaffold allow for the interchange of metabolites, oxygen, and bioactive agents. Further, in a preferred embodiment, the scaffolds of the invention are made of completely biodegradable materials that allow the scaffold to be re-shaped and readily adopted into the surrounding tissue in which it is implanted.

C. Producing the Scaffold

The present invention also provides a method of producing a semi-solid, three-dimensional, biocompatible scaffold by layering one or more sheets of biocompatible A-strip material by a fixed distance from each other; cutting the sheets to provide A-strips of a fixed width, maintaining the parallel A-strips at a fixed distance from each other; and contacting the parallel A-strips with a biocompatible S-strip material under conditions to fill the space separating the A-strips within a layer and between layers to form a semi-solid, three-dimensional, biocompatible and, preferably, biodegradable scaffold. This method of producing the scaffold is preferred when the source material for producing A-strips is available in sheets, for example, submucosa. Biocompatible materials such as polyglycolic acid, polylactic acid, their copolymers, poly(epsilon-caprolactone), polyhydroxybutyrate, polyester copolymers, polycarbonates, polyacrylates, polyanhydrides, polyorthoesters can be formed into sheets, for example, by the methods reported in U.S. Pat. No. 5,723,508. A-strips can comprise synthetic materials which may be combined with a factor that encourages cell attachment.

Alternatively, when the source material for producing A-strips is not available in sheets, a method of producing a semi-solid, three-dimensional, biocompatible scaffold is provided. For example, extracellular matrix gels and liquid matrices (including fluidized submucosa) can be placed (for example, by micro-pipette) onto or into gelatinous layers of alginate to form A-strips according to the appropriate dimensions stated herein, thereby forming a scaffold layer. Also, proteins or peptides (for example, integrins, collagen, laminin, fibronectin, vitronectin, or RGD peptides) that promote cell attachment can be patterned as A-strips onto gelatinous layers of alginate, thereby forming a scaffold layer. These scaffold layers can be sandwiched between layers of alginate (i.e., separating layers) to form a three dimensional scaffold. This method provides an alternative strategy to producing scaffolds with A-strips of cell-adhesive material obtained from non-reconstituted submucosa.

For scaffolds of the invention and the methods of producing those scaffolds, the overall dimensions of the sheet are determined by the intended uses of the scaffold. Scaffolds can be produced that are larger for an area of intended implantation. For manufacturing purposes, it is preferable to produce large scaffolds from which smaller scaffolds can be obtained.

When the cell-adhesive material is in the form of a sheet, the sheet can be coated with one or more of the bioactive agents previously described. When the cell-adhesive material is originally in the form of a liquid, liquid matrix, or gel, one or more bioactive agents can be mixed with the cell-adhesive material prior to forming the strips. In addition, if desired, A-strips of any material can be coated with a physiological solution comprising one or more bioactive agents. Similarly, the S-strips and the separating layers can be coated and/or mixed with one or more bioactive agents.

It is to be understood and expected that variations in the principles of the invention herein disclosed in an exemplary embodiment can be made by one skilled in the art and it is intended that such modifications, changes, and substitutions are included within the scope of the present invention.

D. EXAMPLES

The examples set forth below illustrate several embodiments of the invention. These examples are for illustrative purposes only, and are not meant to be limiting.

Example 1

Method of Making the Scaffold

The instruments used in this example are pictured in FIG. 1.

A porcine small-intestine submucosa (SIS) sheet is obtained (vivoSIS™ cell culture disk, Cook Biotech). The disk has a diameter of 12 millimeters and a nominal thickness of 115 micrometers. The disks are sterile, acellular, and endotoxin free.

Figure 1B:
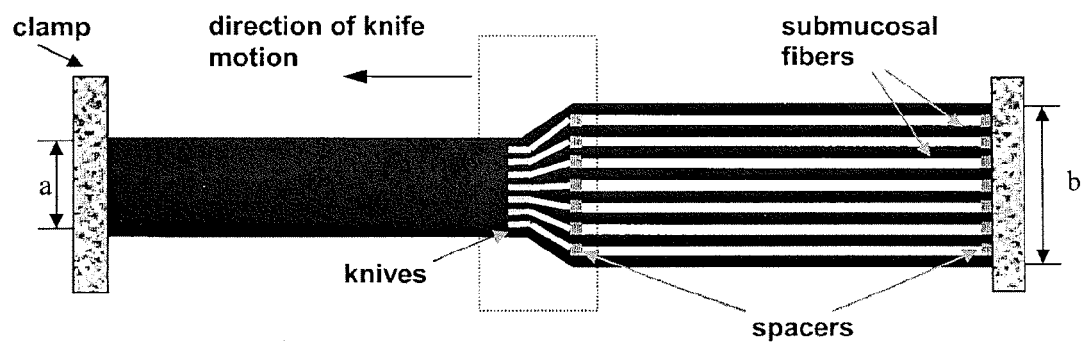

The disks are rehydrated with at least two changes of phosphate buffered saline (PBS) pH 7.4. Upon rehydration, the disks become pliable and easily fold upon themselves. The disks are cut into squares and clamped in layers as shown in FIG. 1A at a fixed distance between layers of about 100 micrometers.

A comb of knives is inserted at one end while another comb of spacers follows the knives. The distances between each knife in the comb of knives are set at a fixed distance of about 30 micrometers. The distance between each spacer in the comb of spacers are set at a fixed distance of about 100 micrometers (width). As the comb of knives cuts through the sheets, the spacers hold the formed strips (A-strips) of submucosal tissue apart (see FIG. 1B). The comb of knives is removed, and the combs of spacers at each end are maintained in place to keep the A-strips separated.

The clamped and spaced A-strips are placed into a mold filled with a 5% sodium alginate solution to submerge the A-strips. After the alginate has sufficiently infiltrated the A-strips, 60 mM calcium chloride solution is added to cross-link the alginate and the A-strips into a semi-solid block. After formation of the semi-solid block, the clamps and the combs of spacers are removed to produce a semi-solid, three dimensional, biocompatible and biodegradable scaffold. Thus, in this example, the alginate that solidifies between the A-strips constitutes the S-strips, and the alginate that solidifies between the A-strip/S-strip layers (scaffold layers) constitutes the separating layers.

Example 2

In Vitro Seeded Scaffolds

The scaffold according to Example 1 is seeded with any cell-type (or combinations of) in vitro. A scaffold is placed in a tissue culture dish or bioreactor with a serum-containing culture medium appropriate for the cells intended for seeding. Generally, cells at a concentration of $1-5 \times 10^6$ cells/ml are added to the dish or bioreactor and incubated for 24-72 hours at 37° C. at 5% $CO_2$.

For example, embryonic stem cell-derived cardiomyocytes are incubated with a scaffold that is 5 millimeters thick (25 layers) and 2 centimeters square with $10^6$ cells in 25 ml of culture medium. This incubation occurs under shaking at 50 rpm at 37° C. at 5% $CO_2$ for 48 hours. This seeded-scaffold is further cultured in media for ten additional days to allow cell spreading.

When bioreactors are used for seeding cells onto scaffolds, some examples are: flasks (static or mixed at 50 or 90 rpm) (Bellco, Vineland, N. J.), 6-well dishes mounted on an xyz gyrator operated at 24 rpm (Shelton, Shelton, Conn.), or two types of rotating bioreactors: the high aspect ratio vessel (HARV) and the slow turning lateral vessel (STLV), both from Synthecon (Houston, Tex.). The mixing properties of these bioreactors are described in Freed, L. E. et al., "Cultivation of cell-polymer tissue constructs in simulated microgravity," *Biotechnol. Bioeng.*, 1995, 46:306-313; Freed, L. E. et al., "Culture of organized cell communities," *Adv. Drug. Deliv. Rev.*, 1998, 33:15-30; Freed, L. E. et al., "Microgravity tissue engineering," *In Vitro Cell Dev. Biol. Anim.*, 1997, 33:381-385; Freed, L. E. et al., "Tissue culture bioreactors: Chondrogenesis as a model system," *Principles of tissue engineering*, 1997, Editors: Langer and Chick, Austin, Tex., pages 151-165; and Vunjak-Novakovic, G. et al., "Effects of mixing on the composition and morphology of tissue engineered cartilage," *J. Am. Inst. Chem. Eng.*, 1996, 42:850-860. Brief protocols for seeding cells onto scaffolds are below, in these protocols, the size of the scaffold is 10-mm by 10-mm (wherein each layer is 10-mm by 10-mm in surface area) by 2-mm (thickness).

For seeding in mixed flasks, scaffolds are pre-wetted with culture medium, threaded onto 4-inch long pieces of stainless steel wire, and positioned using 3-mm long segments of silicone tubing. The wires (up to 4 per flask with 1-2 scaffolds apiece) are embedded into a 5-cm diameter silicone stopper which are placed in the mouth of the flask (6.5-cm diameter, 120 mL volume). Gas exchange occurs via surface aeration. Mixed flasks are stirred at 50 rpm using a 4-cm long, 0.8 cm diameter non-suspended stir bar in a humidified, 5% $CO_2/37°$ C. incubator. After 24 hours, mixed flasks are inoculated with a suspension of cells ($1.3-8\times10^6$ cells/scaffold), and cells are allowed to attach to scaffolds for three days.

For seeding using the xyz gyrator, scaffolds are pre-wetted for 24 hours with medium and inoculated for two hours with a concentrated cell suspension (1 mL containing $8\times10^6$ cells) in 6-well dishes (one scaffold per well) mounted on the xyz generator. Scaffolds are then transferred into mixed flasks (4 needles with 2 scaffolds apiece per flask stirred at 50 rpm) and allowed to seed with the remaining cell suspension from the 6-well dishes for three days.

The culturing space of the HARV is a cylinder with a diameter of 10 cm, a thickness of 1.3 cm, a total volume of 100 mL, and a gas exchange membrane area of 0.8 $cm^2/cm^3$ medium. The HARV is mounted on a base that provides vessel rotation about its central axis and incubator air is pumped over the silicone membrane over gas exchange. Mixing is provided by fluid flow around the scaffolds. For seeding in HARVs, eight scaffolds per vessel are pre-wetted with medium for 24 hours and inoculated with a cell suspension (6 or $8\times10^6$ cells per scaffold). Cells are allowed to attach for three days. During seeding and cultivation, the vessel rotation speed is set at 11-12 rpm in order to maintain constructs freely suspended within the vessel.

The culturing space of the STLV consists of the annular space between two concentric cylinders with diameters of 5.75 and 2 cm. It has a total volume of 110 mL and a gas exchange membrane area of 0.3 $cm^2/cm^3$. Like the HARV, the STLV is mounted on a base that allows vessel rotation (11-12 rpm) and gas exchange. Seeding and cultivation in the STLV is similar to that described for the HARV.

For all the above-methods, medium composition is maintained by regular replacement (same rate in all groups, 50% every other day) and gas exchange between medium and 5% $CO_2$ humidified incubator air maintained at 37° C.

Examples of isolating certain cell-types are shown below.

Rat Cell Isolation and Culturing:

As an example of pre-clinical testing of the scaffold, animal testing can be conducted. For example, the scaffold can be seeded with fetal rat cardiomyocytes. Fetal rat cardiomyocytes are isolated using an enzymatic digestion method (Li, R. K. et al., "Cardiomyocytes transplantation improves heart function," *Annals of Thoracic Surgery*, 1996, 62:654-661; Li, R. K. et al., "In vivo survival and function of transplanted rat cardiomyocytes," *Circulation Research*, 1996, 78:283-288) from 18-day gestational Sprague-Dawley rat heart ventricles (Charles River Canada Inc. Quebec, Canada). Fetal rats are anesthetized with intraperitoneal injection of sodium pentobarbital (30 mg/kg) and the hearts are then excised. The heart tissues are washed with PBS (136.9 mM NaCl, 2.7 mM KCl, 8.1 mM $Na_2HPO_4$, $KH_2PO_4$, 1.5 mM pH 7.3). The tissues are minced and incubated in 10 mL PBS containing 0.2% trypsin, 0.1% collagenase, and 0.02% glucose for 30 minutes at 37° C. Repetitive pipetting of the digested myocardial tissue then isolates the cardiomyocytes. The cells in the supernatant are transferred into a tube containing 20 ml of cell culture medium (Iscove's modified Dulbecco's medium containing 10% fetal bovine serum, 0.1 mmole/L β-mercaptoethanol, 100 units/ml penicillin and 100 µg/ml streptomycin). The tube is centrifuged at 600×g for 5 minutes at room temperature and the cell pellet is resuspended in the cell culture medium for purification.

Adult ventricular cardiomyocytes can also be used to seed the scaffold. Adult rats (Charles River Canada Inc. Quebec, Canada) are anesthetized by intramuscular administration of ketamine hydrochloride (22 mg/kg body weight) followed by an intraperitoneal injection of sodium pentobarbital (30 mg/kg) and the hearts are then excised. Cardiomyocytes are isolated by enzymatic digestion as described above. Adult human ventricular biopsies are similarly enzymatically digested.

Adult atrial cardiomyocytes can be used to seed the scaffold. Rats (Charles River Canada Inc. Quebec, Canada) are anesthetized similarly as above. The atrial appendages are ligated and removed. The atrial tissue is used for cardiomyocyte isolation as described above. Adult human atrial tissue is obtained and similarly enzymatically digested.

Smooth Muscle Cells: Fetal rat cardiomyocytes are isolated using an enzymatic digestion method (Li, R. K. et al., "Cardiomyocytes transplantation improves heart function," *Annals of Thoracic Surgery*, 1996, 62:654-661; Li, R. K. et al., "In vivo survival and function of transplanted rat cardiomyocytes," *Circulation Research*, 1996, 78:283-288) from 18-day gestational Sprague-Dawley rat heart ventricles (Charles River Canada Inc. Quebec, Canada). Fetal rats are anesthetized with pentobarbital (30 mg/kg body weight, intraperitoneal) and the stomachs are then excised. The stomachs are washed with PBS. The stomachs are minced and incubated in 10 ml PBS containing 0.2% trypsin, 0.1% collagenase, and 0.02% glucose for 30 minutes at 37° C. The smooth muscle cells are isolated by repetitive pipetting of the digested myocardial tissue. The cells in the supernatant are transferred into a tube containing 20 ml of cell culture medium (199 medium containing 20% fetal bovine serum, 100 unites/ml penicillin and 100 ng/ml streptomycin). The tube is centrifuged at 600×g for 5 minutes at room temperature and the cell pellet is resuspended in the cell culture medium and cultured.

Adult Smooth Muscle Cells. Adult female rats (Charles River Canada Inc. Quebec, Canada) are anesthetized as described supra. The uterus is removed after occlusion of blood vessels and incisions are closed. The smooth muscle cells are isolated from uterus as described in the paragraph above.

Fetal Fibroblasts. Fetal rat skin biopsies are obtained from 18-day gestational Sprague-Dawley rats. The rats are anesthetized, and fibroblasts from fetal rat skin are isolated, purified and cultured (Mickle, D. A. G. et al., "Water-soluble antioxidant specificity against free radical injury using cultured human ventricular myocytes and fibroblasts and saphenous vein endothelial cells," *Journal of Molecular and Cell Cardiology*, 1990, 22:1297-1304). Briefly, the tissue is washed with PBS and minced. The tissue is then digested with in 10 ml phosphate buffered saline containing 0.2% trypsin, 0.1% collagenase, and 0.02% glucose for 30 minutes at 37° C. The fibroblasts are isolated by repetitive pipetting of the digested myocardial tissue. The cells in the supernatant are transferred into a tube containing 20 ml of cell culture medium (Dulbecco's Modified Essential Medium containing 10% fetal bovine serum, 100 units/ml penicillin and 100 ug/ml streptomycin). The tube is centrifuged at 600×g for 5 minutes at room temperature and the cell pellet is resuspended in the cell culture medium and cultured.

Adult Fibroblasts. Skin biopsies are obtained from adult Sprague-Dawley rats. The fibroblasts are isolated and cultured as described supra.

Adult Endothelial Cells. Adult rat vascular endothelial cells were isolated using an enzymatic digestion method (Mickle et al. 1990) from Sprague-Dawley rat aorta (Charles River Canada Inc. Quebec, Canada). Adult rats are anesthetized as described supra. The aorta is then excised, washed with PBS and incubated in 10 ml PBS containing 0.2% trypsin, 0.1% collagenase, and 0.02% glucose for 30 minutes at 37° C. The blood vessel is washed with cell culture medium (199 medium containing 20% fetal bovine serum, 100 units/ml penicillin and 100 ug/ml streptomycin). The endothelial cells are cultured.

Human Cell Isolation, Culturing and Storage:

Human cardiomyocytes are isolated from atrial appendages and ventricular myocardial biopsies obtained from patients undergoing corrective cardiac surgery. Human myocardium is dissected to remove connective tissue and then minced to pieces less than 1 mm in size. Protocols for culturing are below.

Human Pediatric Cardiomyocytes. Pediatric tissue is digested in an enzymatic digestion solution containing 0.2% trypsin, 0.1% collagenase dissolved in PBS for 15 minutes. No calcium or EDTA was added. Culture medium containing Iscove's modified Dulbecco's medium (IMDM), 10% fetal bovine serum and 0.1 mM β-mercaptoethanol is added in a ratio of 20 volumes culture medium to 1 volume enzymatic digestion solution. The solution is centrifuged at 581 g for 5 minutes. The supernatant is discarded. The cell and tissue pellet is resuspended in culture medium. The isolated cells are cultured on a dish for 5 to 8 days. Cardiomyocytes that migrate from this culture are collected by a Pasteur pipette and cultured with a scaffold.

Human Adult Cardiomyocytes. Different from pediatric tissue digestion, adult human myocardium is digested twice. The second digestion is necessary for the adult tissue due to the increased amount of connective tissue. After the tissue is digested as described above, the solution containing suspended cells is collected. The remaining tissue is incubated with the enzymatic solution for a second time for 10 minutes and the cell suspension is collected. The two collected suspensions are combined. After centrifugation, the cell pellet is resuspended and cultured. The digested tissue fragments in the pellet are collected and cultured for no longer than 2 days (to avoid cell deterioration) and a further enzymatic digestion carried out on the remaining undigested tissue if sufficient cells are not found in the suspensions. Cardiomyocytes are found to grow from the cultured tissue fragments. The cells are isolated and then cultured with the scaffold.

Isolated cells can be cultured with the scaffold immediately or after growth in culture. If isolated cells are to be expanded prior to culturing with a scaffold, then the cells need to be passaged in culture. The cardiomyocytes are cultured in a medium containing IMDM, 10% fetal bovine serum and 0.1 mM β-mercaptoethanol. The cells are subcultured when the culture reaches confluence (i.e., when the cell culture covers the dish surface and the cells begin contacting each other). If the cells are subcultured before reaching confluency, the cells would undergo de-differentiation quickly. If the cells are allowed to become over-confluent, enzymatic digestion yields cell clumps that do not dissociate and would not divide in culture. The subculturing enzymatic solution contains 0.01% trypsin, 0.02% glucose and 0.5 mM EDTA.

Cultured cells can be stored for later incubation with scaffolds. The primary cultures of human cardiomyocytes are stored for future use in liquid nitrogen. The cultured cardiomyocytes are dissociated from the culture plate using the subculturing enzymatic digestion solution. Culture medium is added in a ratio of 5 volumes culture medium to 1 volume digestion solution. The resultant solution is centrifuged at 581 g for 5 minutes. The supernatant is removed and the cell pellet is gently re-suspended in 1 mL IMDM containing 20% fetal bovine serum and 20% glycerol. The solution is transferred to a sterile cryo-vial in a Nalgene freezing container containing isopropranol in its base. The container is stored in a −8° C. freezer container for a period of time that: (a) ensures that the cells reached −80° C.; and (b) prevents over oxidation of the cells. In the present example, the container containing the solution is stored for a minimum of 4 hours and no longer than 8 hours. The long term storage of the cryo-vials containing the cells is in liquid nitrogen.

When the stored cells are to be cultured, the vial is removed from liquid nitrogen and warmed at 37° C. Although 37° C. is found to be preferred, thawing of the cells can take place at other temperatures that allow for rapid yet non-destructive warming. The initial plating of the cells is done in 10 mL of IMDM medium containing 20% fetal bovine serum. The cells are kept in this warming medium for 3 to 5 days to allow the cells to attach firmly to the culture dish before switching to the usual culture medium. The warming medium is IMDM and 20% fetal bovine serum. The cardiomyocytes, cryo-frozen and warmed as described, are morphologically identical to cells that are not frozen and can be successfully subcultured.

Endothelial Cells. Human vascular endothelial cells are isolated from the saphenous vein and aorta obtained from patients undergoing coronary bypass surgery. The endothelial cells are isolated as described for rat endothelial cells.

Smooth Muscle Cells. Human smooth muscle cells are isolated from the saphenous vein after endothelial cell isolation. The remaining tissue is minced and incubated in 10 ml PBS containing 0.2% trypsin, 0.1% collagenase, and 0.02% glucose for 30 minutes at 37° C. Repetitive pipetting of the digested tissue isolates the smooth muscle cells. The cells in the supernatant are transferred into a tube containing 20 ml of cell culture medium (199 medium containing 20% fetal bovine serum, 100 units/ml penicillin and 100 µg/ml streptomycin). The tube is centrifuged at 600×g for 5 minutes at room temperature and the cell pellet is resuspended in the cell culture medium and cultured with a scaffold.

Fibroblasts. Human fibroblasts are isolated from skin biopsies.

Cell Purification. The isolated cardiomyocytes, smooth muscle cells, and vascular endothelial cells are purified by a preplating technique (Simpson, P. et al., "Myocyte hypertrophy in neonatal rat heart cultures and its regulation by serum and by catecholamines," *Circulation Research*, 1982, 51:787-801), which takes advantage of the finding that these cells require a longer time to attach to a cell culture dish than fibroblast cells. The freshly isolated cells are plated on dishes and cultured for 2 hours at 37° C. The supernatant containing the suspended cells are transferred into another dish for further culturing with or without a scaffold.

Another technique for cell purification is the clonal dilution technique. When the cells are seeded at low density for culturing, vial cells form individual colonies. Undesired cell types adjacent to a colony of interest can be necrosed with a sterile needle. Colonies are picked using a sterile pasteur pipette and transferred to new culture dishes for culturing and passaging.

The purity of cultured cardiomyocytes is assessed by immunofluorescent staining for cardiac myosin heavy chain ((Li, R. K. et al., "Cardiomyocytes transplantation improves heart function," *Annals of Thoracic Surgery*, 1996, 62:654-661; Li, R. K. et al., "In vivo survival and function of transplanted rat cardiomyocytes," *Circulation Research*, 1996, 78:283-288)). The cultured cells are fixed with methanol at −20° C. for 15 minutes, washed with PBS, incubated with a monoclonal antibody against MHC for 45 minutes at 37° C., washed three times with PBS for 5 minutes each at room temperature, and then under humid and dark conditions incubated with rabbit anti-mouse IgG conjugated with fluorescein isothiocyanate for 45 minutes at 37° C. The cells are washed with PBS, mounted and photographed using a light and UV microscope. The cardiomyocyte purity is determined by counting the percentage of stained cells in 8 random fields/dish.

The purity of smooth muscle cell culture is determined by immunofluorescent staining for α-smooth muscle cell actin (Sigma). The purity of endothelial cell culture is determined by immunofluorescent staining for factor VII. The purity of fibroblast cell culture is determined morphologically by microscopic examination.

Example 3

Testing of Scaffolds for Cardiac Tissue Repair

To test the scaffolds of the present invention for the ability to promote cell differentiation and growth, a variety of methods are known in the art and can be used. The methods vary relative to the cell seeded in the scaffold, either in vitro or in vivo. This example provides some methods that can be used to test the scaffold's ability to promote cell growth and differentiation for cardiac tissue using cardiomyocyte cells isolated from heart tissue seeded onto scaffolds according to Example 1.

For in vitro scaffolds, medium samples (1 mL) are taken at the end of the seeding period (see Example 2) and every two days during cultivation. pH and partial pressures of oxygen ($\rho$-$O_2$) and carbon dioxide ($\rho$-$CO_2$) are measured immediately after sampling using a gas blood analyzer (Model 1610, Instrumentation Laboratory, Lexington, Mass.) with an accuracy of 0.1% for pH and 2% for $\rho$-$O_2$ and $\rho$-$CO_2$. Cell death and damage during seeding and cultivation are assessed by measuring lactate dehydrogenase (LDH) levels in the supernatant of centrifuged samples of media using a commercial kit (Chiron, East Walpole, Mass.). Concentrations of glucose and lactate in the media are measured using a glucose and L-lactate analyzer (Model 2300 STAT Plus, YSI, Yellow Springs, Ohio).

Scaffold structure is analyzed using light and transmission electron microscopy (TEM). Scaffolds that are taken (either from in vitro cultures or from animals after implantation) for histological analysis are rinsed in PBS, fixed for 10 minutes in 4% glutaraldehyde, incubated for 24 hours in neutral buffered formalin, embedded in paraffin, and cross-sectioned (5 micrometers thick) through the center of the scaffold. Sections are stained with hematoxylin and eosin (H&E) for cells and immunohistochemically for cellular expression of sarcomeric α-actin, muscle desmin, cardiac myosin, cardiac troponin-T, and sarcomeric tropomyosin. Scaffold samples for TEM are fixed in Karnovsky's reagent (0.1 M sodium cacodylate with 2% paraformaldehyde and 2.5% glutaraldehyde, pH 7.4), postfixed in 2% osmium tetroxide, dehydrated in ethanol/propylene oxide, embedded in Poly/Bed812 (Polysciences, Warrington, Pa.), and sectioned (60 nm thick). Sections are stained with lead citrate and uranyl acetate and examined with a transmission electron microscope (JEOL-100CX, JEOL, Peabody, Mass.).

The proper differentiation of cardiac myocytes is assessed by immunohistochemical labeling of muscle specific desmin, muscle specific myosin, cardiac specific troponin-T, and sarcomeric muscle specific tropomyosin. Transmission electron micrographs assess whether the cells have compact mitochondria and myofilaments organized with clearly defined sarcomeres and z lines, as expected for native cardiac muscle cells. The micrographs also show whether intercellular desmosome-like junctions have formed between adjacent cardiac myocytes. To observe whether the cells in the scaffolds contract, videomicroscopy or the unaided eye is able to observe spontaneous and synchronous contractions.

Example 4

Skin Repair

A scaffold with randomly-oriented scaffolding layers can be used to regenerate skin. The scaffold implanted at a site of skin damage without cells. Alternatively, the scaffold is seeded in vitro with fibroblasts and keratinocytes and cultured for the appropriate time before implantation.

Fibroblasts and keratinocytes are two skin cell-types that depend on one another for the proper nutrients, differentiation signals, and production and maintenance of the surrounding extracellular matrix. Keratinocytes and fibroblasts can be isolated from the same skin biopsy. As in Example 2, fibroblasts and keratinocytes are added to cultures containing the scaffolds. A method of producing primary culture keratinocytes from skin biopsies is described in U.S. Pat. No. 5,834,312, Examples 1 and 2, column 10, line 42 to column 14, line 67.

What is claimed:

1. A method for inducing tissue repair and regeneration which comprises surgically implanting a semi-solid three-dimensional biocompatible scaffold at a site in need of tissue repair or growth to thereby induce tissue repair and regeneration, wherein the scaffold is comprised of more than one scaffold layer of alternating attachment-strips (A-strips) and separating-strips (S-strips), the A-strips within each scaffold layer being aligned parallel to each other and the A-strips preferentially promoting cellular attachment to an A-strip over cellular attachment to an S-strip.

2. The method of claim 1, wherein the site in need of tissue repair or growth is an area of myocardial damage or disease.

3. The method of claim 1, wherein the site in need of tissue repair or growth is an area of dermal damage or disease.

4. The method of claim 1, wherein the scaffold is cell free before implantation.

5. The method of claim 1, wherein the scaffold is seeded with cells in vitro before implantation and maintained under conditions sufficient for cells to attach to the scaffold.

6. The method of claim 5, wherein the cells are selected from the group consisting of SP stem cells, Luff stem cells, $Lin^-CD34^-$ stem cells, $Lin^-CD34^+$ stem cells, $Lin^-cKit^+$ stem cells, mesenchymal stem cells, cord blood cells, tissue stem cells, whole bone marrow, bone marrow mononuclear cells, endothelial progenitor cells, skeletal myoblasts, muscle derived cells, go cells, endothelial cells, cardiomyocytes, fibroblasts, smooth muscle cells, genetically modified cells, MyoD scar fibroblasts, pacing cells, teratoma cells, and combinations thereof.

7. The method of claim 6, wherein the cells have been transfected with an expression vector prior to seeding.

8. The method of claim 7, wherein the expression vector is a viral vector.

9. The method of claim 1, wherein the scaffold layers are arranged so the A-strips from one scaffold layer to another are in a substantially parallel orientation.

10. The method of claim 1, wherein the scaffold layers are arranged so the A-strips are in a substantially random orientation.

11. The method of claim 1, wherein the scaffold is biodegradable.

12. The method of claim 1, wherein the A-strips range from about 20 to about 100 micrometers in thickness and from about 20 to about 100 micrometers in width; and wherein the S-strips range from about 20 to about 100 micrometers in thickness, and from about 20 to about 100 micrometers in width.

13. The method of claim 12, wherein the scaffold comprises multiple layers of alternating scaffold layers and separating layers.

14. The method of claim 13, wherein the separating layers range from about 20 to about 200 micrometers in thickness.

15. The method of claim 13, wherein the S-strips and the separating layers have sufficient porosity to allow cell migration throughout the scaffold.

16. The method of claim 13, wherein the separating layers comprise alginate, agarose, gelatin, or combinations thereof.

17. The method of claim 1, wherein the A-strips comprise extracellular matrix material, proteins or peptides that promote cell-attachment, or any combination thereof.

18. The method of claim 17, wherein the extracellular matrix material is from a submucosa, urinary bladder extracellular matrix, bone marrow extracellular matrix, or basement membrane.

19. The method of claim 18, wherein the submucosa is intestine submucosa, stomach submucosa, or liver submucosa.

20. The method of claim 1, wherein the A-strips further comprise one or more bioactive agents.

21. The method of claim 20, wherein the bioactive agent is a vascularization-promoting factor, a cytokine, a growth factor, an enzyme, a hormone, an angiogenesis factor, a vaccine antigen, an antibody, a clotting factor, a regulatory protein, a transcription factor, a receptor, or a structural protein.

22. The method of claim 21, where the bioactive agent is granulocyte-colony stimulating factors (G-CSF), granulocyte-macrophage colony stimulating factor (GM-CSF), stem cell factor (SCF), vascular endothelial growth factor (VEGF), platelet-derived growth factor (PDGF), a transforming growth factor, human growth hormone (hGH), Factor VIII, Factor IX, erthropoietin (EPO), albumin, hemoglobin, alpha-1 antitrypsin, calcitonin, glucocerebrosidase, low density lipoprotein (LDL) receptor, IL-2 receptor, a globin, an immunoglobulin, a catalytic antibody, an interleukin, a chemokine, insulin, insulin-like growth factor 1 (IGF-1), insulinotropin, parathyroid hormone (PTH), leptin, an interferon, a nerve growth factor, epidermal growth factor (EGF), endothelial cell growth factor, endothelial cell stimulating angiogenesis factor (ESAF), angiogenin, tissue plasminogen activator (t-PA), follicle stimulating hormone (FSH), Flt-3 ligand, megakaryocyte growth and development factor (MGDF), or 3-hydroxy-3-methyl glutaryl coenzyme A (HMG CoA) reductase inhibitors.

23. The method of claim 1, wherein the S-strips comprise alginate, agarose, or gelatin.

* * * * *

UNITED STATES PATENT AND TRADEMARK OFFICE
CERTIFICATE OF CORRECTION

| | | |
|---|---|---|
| PATENT NO. | : 7,579,189 B2 | Page 1 of 1 |
| APPLICATION NO. | : 12/111482 | |
| DATED | : August 25, 2009 | |
| INVENTOR(S) | : Freyman et al. | |

It is certified that error appears in the above-identified patent and that said Letters Patent is hereby corrected as shown below:

Title Page, Item 73

Assignee should be changed from "Scimed Life Systems, Inc." to --Boston Scientific Scimed, Inc.--.

Signed and Sealed this
Thirty-first Day of May, 2011

David J. Kappos
*Director of the United States Patent and Trademark Office*